(12) United States Patent
Mechlenburg et al.

(10) Patent No.: US 7,367,935 B2
(45) Date of Patent: May 6, 2008

(54) MUSCLE STIMULATING DEVICE AND METHOD FOR DIAGNOSING AND TREATING A BREATHING DISORDER

(75) Inventors: Douglas M Mechlenburg, Murrysville, PA (US); Rodger P Gaumond, State College, PA (US)

(73) Assignees: RIC Investments, LLC, Murrysville, PA (US); The Penn State Research Foundation, University Park, PA (US)

( * ) Notice: Subject to any disclaimer, the term of this patent is extended or adjusted under 35 U.S.C. 154(b) by 752 days.

(21) Appl. No.: 10/811,592

(22) Filed: Mar. 29, 2004

(65) Prior Publication Data

US 2004/0193003 A1    Sep. 30, 2004

Related U.S. Application Data

(60) Continuation of application No. 09/761,788, filed on Jan. 17, 2001, now Pat. No. 6,770,022, which is a division of application No. 09/173,871, filed on Oct. 16, 1998, now abandoned.

(60) Provisional application No. 60/062,288, filed on Oct. 17, 1997.

(51) Int. Cl.
  *A61N 1/00* (2006.01)
(52) U.S. Cl. ....................................... 600/13
(58) Field of Classification Search ................ 128/899, 128/200.24; 607/42; 600/9, 11–14
  See application file for complete search history.

(56) References Cited

U.S. PATENT DOCUMENTS

| | | | |
|---|---|---|---|
| 3,480,010 A | | 11/1969 | Crossley |
| 4,340,038 A | * | 7/1982 | McKean ...................... 600/12 |
| 4,519,400 A | | 5/1985 | Brenman et al. |
| 4,669,459 A | | 6/1987 | Spiewak et al. |
| 4,788,533 A | | 11/1988 | Mequignon |
| 4,827,935 A | | 5/1989 | Geddes et al. |

(Continued)

FOREIGN PATENT DOCUMENTS

EP    0 743 076 A1    11/1995

(Continued)

OTHER PUBLICATIONS

Alan R. Schwartz, "Hypoglossal Nerve Stimulation in Obstructive Sleep Apnea", New Therapeutic Approaches for Obstructive Sleep Apnea, Johns Hopkins Sleep Disorders Center, APSS Post-Graduate Course, May 30, 1995.

(Continued)

*Primary Examiner*—Samuel G Gilbert
(74) *Attorney, Agent, or Firm*—Michael W. Haas

(57) ABSTRACT

A device and method for magnetic stimulation of muscles for the relief of a breathing disorder, such as obstructive sleep apnea is disclosed. Magnetic stimulation is used to stimulate muscles which serve to stabilize the upper airway of an individual whose nocturnal apneic events are related to diminished muscle tone. In one embodiment, a sensor monitors a physiologic characteristic of the patient, a coil is energized to stimulate the appropriate muscles associated with the upper airway, a power supply provides power for energizing the coil, and a control system controls the application of power to the coil based on the output of the sensor. A passive probed is provided in the patient to focus the magnetic field produced by the coil.

10 Claims, 11 Drawing Sheets

U.S. PATENT DOCUMENTS

| | | | |
|---|---|---|---|
| 4,830,008 A | 5/1989 | Meer |
| 4,850,340 A | 7/1989 | Onishi |
| 5,047,005 A | 9/1991 | Cadwell |
| 5,061,234 A | 10/1991 | Chaney |
| 5,078,674 A | 1/1992 | Cadwell |
| 5,123,425 A | 6/1992 | Shannon et al. |
| 5,123,898 A | 6/1992 | Liboff et al. |
| 5,158,080 A | 10/1992 | Kallok |
| 5,190,053 A | 3/1993 | Meer |
| 5,193,539 A | 3/1993 | Schulman et al. |
| 5,193,540 A | 3/1993 | Schulman et al. |
| 5,211,173 A | 5/1993 | Kallok et al. |
| 5,265,624 A | 11/1993 | Bowman |
| 5,295,490 A | 3/1994 | Dodakian |
| 5,312,439 A | 5/1994 | Loeb |
| 5,335,657 A | 8/1994 | Terry et al. |
| 5,344,384 A | 9/1994 | Ostrow et al. |
| 5,483,969 A | 1/1996 | Testerman et al. |
| 5,485,851 A | 1/1996 | Erickson |
| 5,549,106 A | 8/1996 | Gruenke et al. |
| 5,549,655 A | 8/1996 | Erickson |
| 5,591,216 A | 1/1997 | Testerman et al. |
| 5,697,076 A | 12/1997 | Troyk et al. |
| 5,766,124 A | 6/1998 | Polson |
| 5,792,040 A | 8/1998 | Koeneman et al. |
| 5,792,067 A | 8/1998 | Karell |
| 5,814,089 A | 9/1998 | Stokes et al. |
| 5,891,158 A | 4/1999 | Manwaring et al. |
| 5,945,762 A | 8/1999 | Chen et al. |
| 5,979,456 A | 11/1999 | Magovern |
| 5,988,171 A | 11/1999 | Sohn et al. |
| 6,099,459 A | 8/2000 | Jacobson |
| 6,132,384 A | 10/2000 | Christopherson et al. |
| 6,240,316 B1 | 5/2001 | Richmond et al. |
| 6,345,202 B2 * | 2/2002 | Richmond et al. ............ 607/42 |
| 6,604,529 B2 * | 8/2003 | Kim ........................... 128/899 |

FOREIGN PATENT DOCUMENTS

| | | |
|---|---|---|
| EP | 0 494 787 B1 | 3/1996 |
| EP | 0 702 977 A2 | 3/1996 |
| SU | 1533-140 A | 3/1990 |
| WO | WO-98/37926 A1 | 9/1998 |
| WO | WO-98/43700 A1 | 10/1998 |
| WO | WO-98/43701 A1 | 10/1998 |

OTHER PUBLICATIONS

Richard S. Schwartz et al., "Effects of Electrical Stimulation to the Soft Palate on Snoring and Obstructive Sleep Apnea", Dec. 20, 1995, pp. 1-17.

Jali Medical, Inc., Newton, MA 02159; "Magstim 200 and Accessories Price List," May 1994.

Geddes et al., "Magnetic (Eddy-Current) Electroventilation in the Dog," Annals of Biomed. Engr., vol. 21, Jun. 1993, 193-197.

Geddes et al., "Electrically Produced Artificial Ventilation," Medical Instrumentation, vol. 22, No. 5, Oct. 1988, 263-271.

The Dobelle Institute, Inc., New York, NY; "Breathing Pacemakers" (as advertised in the New England Journal of Medicine, Neurosurgery, The Journal of Neurosurgery and Paraplegia News), Nov. 1995; 3 pages.

Geddes et al., "Artificial Respiration in the Dog by Percutaneous, Bilaterial, Phrenic Nerve Stimulation," Am. J. Emerg. Med., vol. 9, No. 6, Nov. 1991, 527-529.

Mouchawar et al., "Magnetic Electrophrenic Nerve Stimulation to Produce Inspiration," Annals of Biomed. Engr., vol. 19, 1991, 219-221.

Jalinous, "Guide to Magnetic Stimulation," Updated Oct. 1993; 37 pages.

Voorhees et al., "Technical Note: Magnetically Induced Contraction of the Inspiratory Muscles in Dog" J. Clin. Engr., vol. 15, No. 5, Sep./Oct. 1990, 407-408.

Van de Graaff et al., "Respiratory Function of Hyoid Muscles and Hyoid Arch," American Physiological Society, 1984; 197-204.

Schnall et al., "Dilatory Effects of Upper Airway Muscle Contraction Induced by Electrical Stimulation in Awake Humans," American Physiological Society, 1995; 1950-1956.

Geddes et al., "Electroventilation," J. Emerg. Med., vol. 3, No. 4,.Jul. 1985, 337-339.

Cameron et al., "Micromodular Implants to Provide Electrical Stimuation of Paralyzed Muscles and Limbs," IEEE Transactions on Miomedical Engineering, vol. 44, No. 9, Sep. 1997, pp. 781-790.

Mouchawar, et al., "Short Communication Magnetic Electrophrenic Nerve Stimulation to Produce Inspiration," Annals of Biomedical Engineering, vol. 19, 1991, pp. 219-221.

* cited by examiner

MUSCLE STIMULATING DEVICE AND METHOD FOR DIAGNOSING AND TREATING A BREATHING DISORDER

CROSS REFERENCES TO RELATED APPLICATIONS

This is a Continuation of U.S. patent application Ser. No. 09/761,788, filed on Jan. 17, 2001, now U.S. Pat. No. 6,770,022, under 35 U.S.C. § 120, which is a Divisional of U.S. patent application Ser. No. 09/173,871, filed on Oct. 16, 1998, under 35 U.S.C. § 120, abandoned, which claims priority under 35 U.S.C. § 119(e) from U.S. Provisional Patent Application No. 60/062,288 filed Oct. 17, 1997.

BACKGROUND OF THE INVENTION

1. Field of the Invention

The present invention pertains to an apparatus and method for noninvasive stimulation of muscles in the upper airway to diagnose and/or treat a breathing disorder, such as obstructive sleep apnea In particular, the present invention pertains to a magnetic stimulation device and a method of using the device to apply pulsed magnetic fields to the muscles in the neck area of a patient to induce tension in such muscles, thereby relieving the obstructive sleep apnea caused by a relaxation of such muscles. By measuring an awake patient's compliance in the presence and absence of the magnetic stimulation, the likelihood that the patient suffers from obstructive sleep apnea can be determined.

2. Description of the Related Art

Obstructive sleep apnea (OSA) is a condition in which sleep is repeatedly interrupted by an inability to breathe due to an obstructed upper airway segment. Those afflicted with OSA experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during wakefulness, as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

Studies of the mechanism of collapse of the airway suggest that during some stages of sleep, there is a general relaxation of the muscles which stabilize the upper airway segment. This general relaxation of the muscles is believed to be a factor contributing to OSA.

Existing therapeutic remedies for treating OSA include the surgical removal of deformed, loose or swollen structures in the upper airway. It is also known to apply positive air pressure at the mouth and/or nose of the patient to "splint" the airway, thereby maintaining an open passage to the lungs. In addition, pharmacologic solutions have also been pursued.

Neither of these therapies is successful in all cases. Surgical relief is invasive, introduces a potential for surgical complications and is appropriate in only a small percentage of cases. On the other hand, the nasal mask needed to apply a positive air pressure is not tolerated by some OSA patients. Pharmacological therapy has been, in general, less than satisfactory, and side effects are frequent.

It is also known to treat OSA by electrically stimulating the musculature in the neck area associated with the upper airway. One such method of electrically stimulating the muscles in the upper airway area of a patient involves placing an electrode in direct contact with a surface of the patient and passing a current through the surface tissues of the patient contacting the electrode. For example, an intraoral appliance has been developed that applies electrical currents to the tongue, causing it to contract, thereby helping to clear the airway. Another known appliance applies electrical stimulation to the exterior surface of the patient's neck below the chin to induce contraction of the upper airway muscles.

Electrical stimulation using surface mounted electrodes creates relatively large current densities at the site of the electrodes. Because these current densities are disposed at the surface of the patient, which also contains a relatively large number of nerve endings, such electrical stimulation devices can cause unpleasant or painful sensations, possibly arousing the user from sleep.

It is also known to apply electrical stimulation to the muscles of the upper airway via electrodes implanted in the patient. Subcutaneous electrodes have the benefit of being positioned adjacent to the muscle or nerve to be stimulated to focus the electrical energy on that muscle/nerve while reducing the amount of collateral tissues effected by the high current densities near the electrode. There are also typically fewer nerve endings deep within the patient than at the surface. Thus, electrical stimulation using implanted electrodes reduces the likelihood that the electrical stimulation will induce an unpleasant or painful sensation in the patient. However, electrical muscle stimulation utilizing implanted electrodes requires surgical intervention, the permanent presence of foreign materials within the patient's neck tissue, and at least one electrical connection protruding from the patient. Consequently, there is a potential for infection or irritation at the surgical site and at the site where the electrode protrudes through the surface of the patient.

SUMMARY OF THE INVENTION

Accordingly, it is an object of the present invention to provide a device for stimulating the muscles in the upper airway area for the treatment of OSA that does not suffer from the disadvantages associated with the above-described conventional OSA treatments. This object is achieved by providing a non-invasive device for magnetically stimulating the muscles that stabilize the upper airway to cause them to contract. Because the stimulation is via magnetic induction, which is capable of stimulation of deep muscular structures, the present invention does not generate large currents at the skin. Therefore, it is less painful than surface electrode electrical stimulation devices.

The muscle stimulator for applying a magnetic field to at least one muscle or muscle group associated with an upper airway in a patient experiencing obstructive sleep apnea to induce tension in that muscle or muscle group to relieve the obstructive sleep apnea includes a plurality of loops of electrical wire and a power supply that selectively provides electrical power to the plurality of loops. Applying power to the loops produces the magnetic field used to stimulate the targeted muscles. A sensor monitors a condition of the patient associated with the obstructive sleep apnea, such as the snoring sounds produced by the patient or the patient's respiration, to determine when to initiate stimulation and how to change the intensity of the stimulation, if necessary, during the therapy process. A control unit receives signals output by the sensor and controls the application of electrical power from the power supply to the plurality of loops of electrical wire. A positioning appliance secures the plurality of loops of electrical wire to the patient at a position relative to the targeted muscle or muscle group such that the magnetic field produced by applying electrical power to the plurality of loops of electrical wire induces tension in that muscle or muscle group to relieve the obstructive sleep apnea.

It is a further object of the present invention to minimize the heat experienced by the patient as a result of using the magnetic stimulator. To that end, the present invention includes an insulating material between the patient's skin and the coil. In addition, the temperature of the coil is monitored by a temperature sensor and the power to the coil is controlled based on the temperature of the coil so that excessive heat is not generated in the coil. Also, portions of the coil are maintained as far from the patient as possible while still permitting the magnetic stimulator to provide its therapeutic effect.

It is a still further object of the present invention to control the application of magnetic energy to the patient based on the condition of the patient. To achieve this object, sensors are provided to monitor the condition of the patient. For example, sensors are used to determine whether the patient is snoring and/or experiencing an apneic event. If so, the coil is energized to treat the OSA. Energizing the coil can also be synchronized with the patient's respiration so that stimulation begins within a predetermined window during the patient's respiratory cycle, such as at the onset of inspiration or at a period offset therefrom. Also, the present invention contemplates using the conditions of the patient, such as the presence of snoring, an apneic event and/or the respiratory patterns of the patient, to regulate the intensity of the magnetic stimulation. For example, the more prevalent the apneic events, the greater the level of stimulation. Conversely, a reduced number of apneic events results in a reduced level of stimulation. In this manner, only the necessary level of magnetic energy is applied to the patient.

It is a further object of the present invention to provide a method of using the device discussed above to apply a magnetic field to at least one muscle group associated with an upper airway of a patient experiencing obstructive sleep apnea to induce tension in that muscle group to treat the obstructive sleep apnea.

It is yet another object of the present invention to provide a system and method for diagnosing whether a patient is likely to suffer from OSA. This object is achieved by providing a system that measures a compliance of the patient to obtain a first compliance level, applies a magnetic field to at least one muscle group associated with an upper airway of the patient, measures the compliance while applying the magnetic field to obtain a second compliance level, and compares the first compliance level to the second compliance level. The smaller the difference between the first and second compliance levels, the more likely the subject suffers from obstructive sleep apnea.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
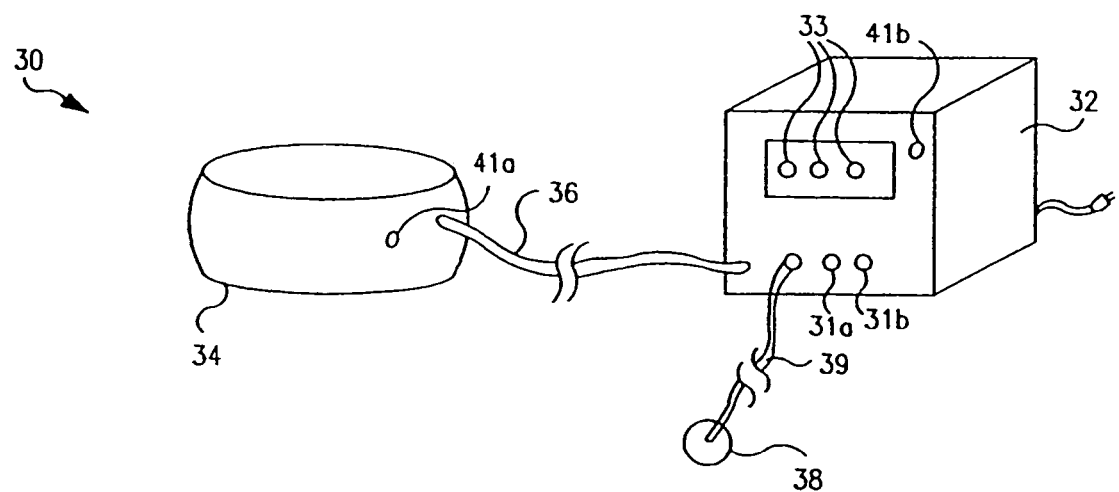
FIG. 1 is a perspective view of a magnetic stimulator according to the principles of the present invention.
Figure 2:
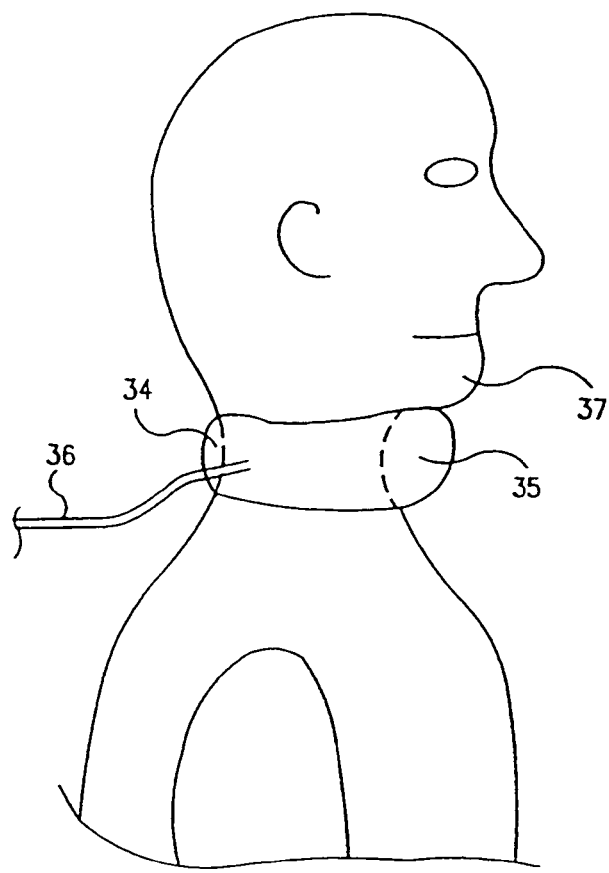
FIG. 2 is a side view of a person wearing the collar illustrated in FIG. 1.

FIG. 1 illustrates a first embodiment of a magnetic stimulator 30 according to the principles of the present invention. Magnetic stimulator 30 includes a control unit 32 and a collar 34 coupled to control unit 32 via a flexible cable 36. Collar 34 attaches to the patient's neck, as shown in FIG. 2, such that a portion 35 of collar 34 containing at least one magnetic field generating coil is disposed directly under the patient's chin 37. Control unit 32 receives signals from at least one sensor, such as sensor 38, which is connected to control unit 32 via a cable 39. Control unit 32 energizes the coil in collar 34 to produce a time varying electrical current that creates a changing magnetic field, whose rapidly increasing flux, in turn, creates a spacially varying electric field having a gradient that is maximized at specific muscles and/or muscle nerves in the upper airway. In short, the changing magnetic field produced by energizing the coil with a time varying current, such as a pulse train, induces tension in the muscles pulling the obstructing tissue from the patient's airway, thereby relieving the obstructive sleep apnea.

In the embodiment illustrated in FIG. 1, power is provided to control unit 32 from an external power supply. It is to be understood, however, that batteries or other internal power storage devices can be provided in place of, or in addition to, the external power source to energize the coil in collar 34, sensor 38, and/or the components within control unit 32.

In the illustrated embodiment, control unit 32 includes manually operable actuating mechanisms 33, such as buttons, dials, knobs or switches, for performing functions such as activating and deactivating the unit, setting the ranges for the output field strength and/or duration, setting threshold values, setting operating modes, and conducting diagnostic routines on the magnetic stimulator. The present invention also contemplates that one control unit can be used in conjunction with a plurality of sensors, a plurality of collars, and/or a plurality of collar-sensor combinations. If one control unit is being used in conjunction with a plurality of sensors, a plurality of collars, and/or a plurality of collar-sensor combinations, that control unit would include additional input/output interfaces 31a for connecting the additional sensors, collars, and or collar-sensor combinations thereto.

The control unit can also be configured with any appropriate input/output interface for exchanging data between the control unit and an external source. For example, one or more interfaces 31b can be provided for accessing, modifying, or downloading data stored in the control unit. Such data exchange interfaces can include, but are not limited to, an RS-232 port, modem, coaxial, optical fiber, rf, infrared, ultrasonic, or other interfaces that permit data exchange between the control unit and the external device. For example, data can be provided to the control unit using manual input devices, such as knobs, switches, buttons, and/or keypads coupled to or integral with the control unit. Data can also be provided to, modified or extracted from the control unit using an external computer that communicates with the control unit using an appropriate interface.

In the illustrated embodiment, control unit 32 and collar 34 include warning devices, such as an audio indicator 41a and a visual indicator 41b, that inform the user, or a person monitoring the user, of the condition of the patient and/or magnetic stimulator 30. For example, an audio or visual warning can be generated if the patient has stopped breathing for a predetermined period of time, has begun or has stopped snoring, and/or has removed or put on the collar. Of course, an appropriate sensor or plurality of sensors for sensing such conditions must be provided.

As noted above, the present invention also contemplates providing warning signals indicative of the status of the magnetic stimulator. For example, an audio or visual warning signal can be generated if the coil in the collar exceeds a predetermined temperature, if the power provided to the control unit, the sensors, or the collar has been shut off, falls below a predetermined level or exceeds a predetermined level, if the sensors or the coil are not working, have become disconnected or fail to communicate with the control unit, and/or if there is a short in the coil, sensors and/or control unit.

In addition to or in place of the relatively simple audio/visual warning indicators 41a and 41b, other warning devices can be provided. For example, control unit 32 can include circuitry for notifying a remotely located third party of the existence of the condition causing the warning, using, for example, signals communicated via telephone lines. Furthermore, the warning signals, as well as other signals indicative of the condition of the patient and/or the magnetic stimulator that do not constitute a warning, can be provided to a display device (not shown) such as a monitor or LED. Such a display system may be particularly beneficial in a sleep lab setting where a single control unit is being used to monitor and magnetically stimulate a plurality of patients under the supervision of a sleep lab technician.

It is to be further understood, that the collar, control unit and sensors need not be separate elements. For example, as discussed in greater detail below, the sensor can be disposed on the collar so that the collar-sensor combination functions as a unit. In addition, the control unit can also be provided on the collar so that most of the components of the magnetic stimulation system, i.e., the sensors, coil, and control unit are contained in one assembly that is worn by the patient. Depending on the power requirements, the power supply can also be provided in that assembly, further minimizing the number of components that the patient has to be concerned with when using the magnetic stimulator.

Figure 3:
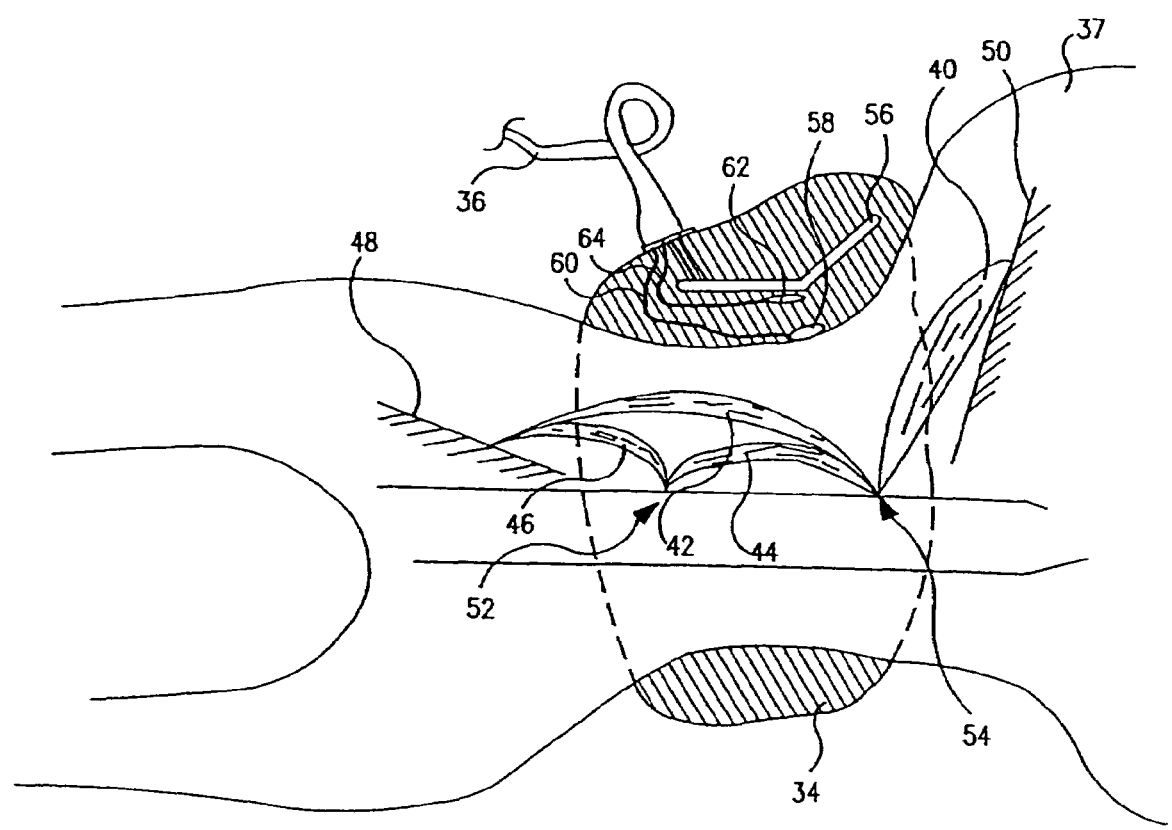
FIG. 3 is another side view, partially in section, showing in greater detail the collar of FIG. 1 positioned on the patient.

As shown in FIG. 3, which is a schematic illustration of the muscles associated with the upper airway, the muscles targeted for stimulation are the geniohyoid muscle 40 under the chin 37, the left and right sternohyoid muscles 42, the left and right thyrohyoid muscles 44, and the left and right sternothyroid muscles 46. The sternothyroid, sternohyoid and thyrohyoid muscles are arrayed in pairs on either side of the trachea mid-line. However, for ease of illustration, only one of each of these muscles is illustrated in FIG. 3, which also shows the respective attachments of these muscles to the sternum 48, mandible 50, thyroid cartilage 52 and hyoid arch 54.

These muscles have been identified by the present inventors as being particularly relevant to the onset and prevention of OSA because, when contracted, these muscles brace the hyoid arch and increase tension in the tissue surrounding the upper airway, thereby preventing obstruction of the airway. It has been discovered that during sleep, in some patients, the relaxation of these muscles decreases the hyoid arch support and the support of the tissue surrounding the upper airway to an extent sufficient to result in obstruction of the upper airway, thereby causing those patients to suffer from OSA. The present invention avoids this consequence by magnetically stimulating the geniohyoid, sternothyroid, sternohyoid and thyrohyoid muscles so that they provide the proper level of support even while the patient is asleep.

It is to be understood that while the geniohyoid, sternothyroid, sternohyoid and thyrohyoid muscles are the primary muscles that the present invention contemplates stimulating, this invention is not limited to stimulation of these particular muscles. Other muscles or muscle groups, instead of or in addition to these muscles, can be targeted for stimulation. For example, the genioglossus, the stylohyoid muscle and hyoglossus muscle attaching to the rostral surface of the hyoid cartilage, and the omohyoid muscle, which attaches below the hyoid cartilage, are possible targets for stimulation, so long as any such stimulation furthers the goal of supporting the tissues surrounding the upper airway to reduce and/or minimize the occurrence of OSA.

As shown in FIG. 3, when properly worn by the patient, collar 34 positions a coil 56 in an overlying relationship with the geniohyoid, sternothyroid, sternohyoid and thyrohyoid muscles so that the magnetic field generated by passing a current through coil 56 is specifically targeted on these muscles and/or on the nerves controlling the contraction of these muscles. Collar 34 encircles the patient's neck and is made from a comfortable, semi-flexible material. Collar 34 must be flexible enough to be fitted on and comfortably worn by the patient. However, it must be rigid enough to maintain coil 56 in an appropriate position relative to the targeted muscles so that at a localized concentration of the magnetic field occurs at these muscles even if the patient moves during sleep. The collar is also preferably made from a heat insulating material so that heat generated by the current passing through the coil is prevented from reaching the patient. To further achieve this goal, an additional thermo-insulating material or layers of such material can be provided between coil 56 and the inside surface of collar 34.

It is to be understood that the present invention is not limited to the illustrated configuration of the collar. Quite the contrary, the present invention contemplates any positioning device that locates and maintains the coil in an appropriate position to stimulate the targeted muscles while minimizing heat transfer to the patient. For example, the present invention contemplates that coil 56 can be attached to the patient using an adhesive, for example, without the need for a collar. In which case, an insulating material can be provided between the coil and the patient that is also attached to the patient using any suitable method, such as adhesive.

In one embodiment of the present invention, magnetic stimulator 30 is dynamically controlled so that stimulation is only applied to the patient's upper airway muscles as required in order to counteract the occurrence of OSA. For this reason, sensors, such as sensor 38 in FIG. 1, are provided to detect the onset of OSA by monitoring characteristics of the patient indicative of this event. It is to be understood, however, that other characteristics of a patient that may or may not relate to the onset of OSA, such as body temperature, can be monitored by the sensors and the control unit of this invention to provide more general information on the condition of the patient, which may be useful in determining the condition of the patient throughout the stimulation process. This information may be particularly useful in the sleep lab situation or hospital. Another patient characteristic that can be monitored is the blood gas levels, such as the oxygen and/or $CO_2$ levels. Blood gas information can be used to monitor the effectiveness of the stimulation or to control the activation and/or deactivation of such stimulation.

In one embodiment of the present invention, sensor 38 is an acoustic sensor that is positioned near or on the patient to sense the onset of inspiration-induced upper airway collapse, which manifests in the form of snoring sounds emitted by the patient. Such snoring sounds are typically produced by the unstable airway vibrating during inspiration, and the occurrence of a snore and its increase in prominence in successive breaths can indicate the onset of an apneic event. The increase in snore intensity on successive inspirations warns of the impending need for magnetic stimulation on a subsequent inspiration. Thus, detecting the occurrence of a snore and controlling the stimulator based thereon is an effective method for dynamically controlling stimulation so that it is only applied to the patient as necessary to counteract the occurrence of OSA.

In another embodiment of the present invention, one or more sensors are provided to detect the respiratory patterns of the patient. This can be accomplished, for example, by monitoring the airflow in the patient's airway and/or the expansion and contraction of the chest, thorax and/or abdomen. The magnetic stimulator can be activated during a specific window in the patient's respiratory cycle, such as at the onset of inspiration or at a period offset therefrom, to prevent or threat OSA. The present invention also contemplates monitoring the patient's EMG activity and stimulating the patient based thereon.

In the embodiment illustrated in FIG. 1, sensor 38 is a separate component from collar 34. As such, it must be separately mounted on the patient. This configuration is advantageous in that it permits one or more sensors to be located at various spaced apart locations on the patient unrelated to the other elements of the magnetic stimulator, such as the collar, for monitoring the same or different conditions of the patient from various anatomical locations. For example, the patient's heart rate can be monitored from sensors located on the front and back of the patient's torso.

It has been determined through clinical testing that the sound frequencies that correspond to upper airway narrowing are in the range of 20-250 Hz. To optimize the detection of upper airway sounds in this bandwidth, it is preferable to locate an acoustic sensor on the external surface of the patient's throat. In the embodiment illustrated in FIG. 3, an acoustic sensor 58 is fixed at the inside surface of collar 34 so that sensor 58 is positioned at the external surface of the patient's throat when collar 34 is worn by the patient. This configuration also enables both the coil and the sensor to be properly mounted on the patient by merely donning collar 34, thereby avoiding the need to place the collar and sensor on the patient separately. Sensor 58 is coupled to control unit 32 via wiring 60 and transmits a signal indicative of the sounds generated in the patient's upper airways to the control unit.

While the sensor described above detects throat vibration using an acoustic sensor, it is to be understood that other sensors capable of detecting the onset of an upper airway event are within the scope of the present invention. Examples of other suitable sensors include airflow sensors, pressure sensors, an electromyogram (EMG) as a measure of muscular effort, and fiber-optic vibration sensors. Such sensors can be operatively coupled to the collar, the control unit or can be wireless. Furthermore, while only one patient condition monitoring sensor is illustrated in collar 34 of FIG. 3, other sensors in addition to or in place of sensor 58 can be provided at the same locations or at other locations than that illustrated in FIG. 3. For example, an acoustic sensor may be provided on an exposed surface of collar 34 instead of or in addition to audio sensor 58. Also, a pressure sensor and/or an EMG sensor, separate from collar 34, may be fixed to the patient for monitoring inspiration or muscle effort, respectively. The data from the combination of sensors can be compared and analyzed together to detect more accurately the onset of an upper airway event that is indicative of the occurrence of OSA.

Collar 34 in FIG. 3 also includes a second sensor 62 in the form of a thermistor probe to monitor the temperature of coil 56. Sensor 62 enables the control unit to prevent electrical energy from being provided to coil 56 in the event the heat generated by energizing the coil exceeds a predetermined threshold. Sensor 62 is connected to the control unit via electrical wiring 64 within the collar. Electrical wiring 60 and 64, as well as the electrical wiring providing power to coil 56, can be provided in the same flexible tube 36 so that only one cable and one interface are needed between the collar and the control unit.

In the embodiment illustrated in FIG. 3, cable 36 connects coil 56 to a power supply. It is to be understood, however, that other methods of providing power to coil 56 are contemplated by the present invention. For example, collar 34 can contain an internal power supply for energizing coil 56, thus eliminating the need for a dedicated power supply line between the control unit and the coil. Such a configuration requires a communication link between the control unit and the power supply system in the collar so that activation, deactivation and energy levels provided to the coil can be controlled. Such a communication link can be hardwired or wireless.

It is to be further understood that the data link between the control unit and sensors 58 and 62 can be hardwired, as shown in FIG. 3, or wireless, so long as data is transmitted by the sensors to the control unit. Wireless communication, which can be rf, infrared, or ultrasonic, for example, requires that a power supply be provided on collar 34 for powering sensors 58 and 62. Furthermore, data can be sent from sensors 58 and 62 automatically, for example at regular timed intervals, or upon a request from the control unit. This latter technique, however, requires that sensors 58 and 62 have the ability to receive and process commands from the control unit and that the control unit have the ability to transmit and process these commands and the associated responses.

Figure 4:
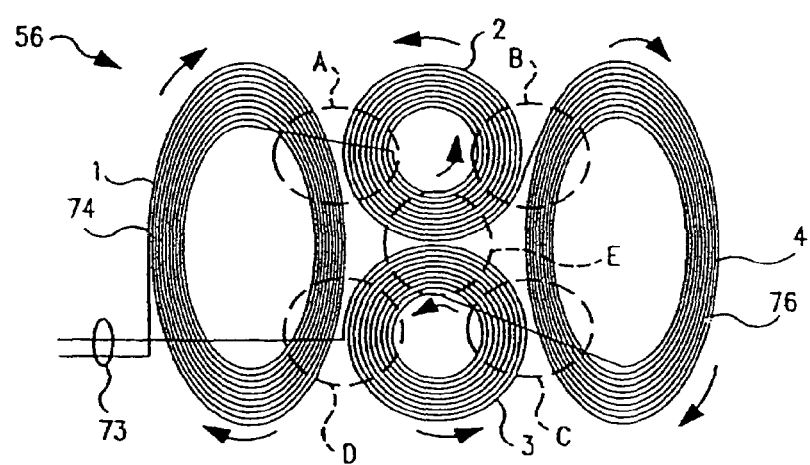
FIG. 4 is a plan view of a first embodiment of the coil disposed in the collar portion of the magnetic stimulator.

Details of a first embodiment of coil 56 and the general position of coil 56 relative to the patient are discussed below with reference to FIGS. 4-6. As shown in FIG. 4, coil 56 includes a plurality of adjacently located loops, identified 1, 2, 3, and 4. Loops 1-4 each have one or more turns, and the entire coil is wound from a continuous length of electrical wire, such as copper or silver, so that only one pair of terminals 73 are needed to energize all four loops. An electrical insulation separates each turn in each loop from the other turns in that loop. Each loop can be configured so that the wires in each turn of that loop lie in the same plane, as shown in FIG. 4. However, other configurations for the wires in the loops are possible. For example, the turns in a loop can be stacked one on another, or twisted or braided together.

The structure of coil 56 and the direction of current flow through the loops, as shown by the arrows in FIG. 4, is selected to optimize the magnetic field intensity at certain locations relative to coil 56. In particular, increased magnetic field intensities are created in an area below coil 56 corresponding to areas A, B, C, and D between adjacent loops at which currents summate. In other words, an area of increased magnetic field strength is created in an area below the coil where two loops are adjacent one another and where the currents flow through these adjacent loops in the same direction. In FIG. 4, the currents in loops 1 and 2 at area A are flowing in the same direction, e.g., downward relative to the top of this diagram. Thus, there is an area of increased magnetic field strength in a region below coil 56, i.e., in a direction toward the page, corresponding to area A. This increased magnetic field strength is caused by a summation of magnetic fields generated by loops 1 and 2. Similar areas of increased magnetic fields are created at areas corresponding to areas B, C, and D.

In the embodiment illustrated in FIG. 4, four areas of increased magnetic field strength are created in order to target the stimulating effect provided by the present invention at four regions of the patient's neck. These regions correspond to the locations of the geniohyoid 40, sternothyroid 46, sternohyoid 42 and thyrohyoid 44 muscles. See FIG. 5. By providing the specific configuration for coil 56, the present invention stimulates only muscles deemed to be particularly suited to maintaining an unobstructed airway.

In the embodiment of the present invention illustrated in FIG. 3, in which sensors 58 and 62 are provided on or in collar 34, it is desirable to locate these sensors in an area where the magnetic field intensity is at a minimum. Such an area is identified as area E in FIG. 4 and corresponds to a position between adjacent loops 2 and 3 where the current in each loop are flowing in opposite directions.

Figure 5:
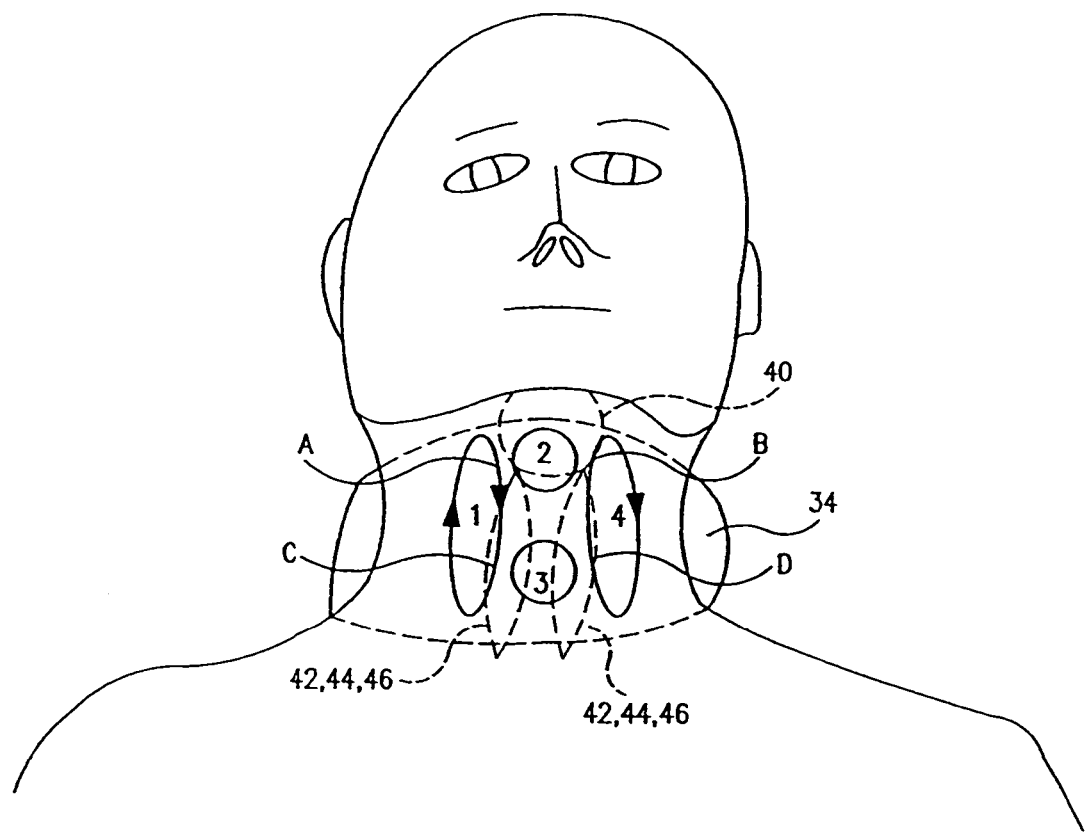
FIG. 5 is a front view illustrating the superposition of the coil illustrated in FIG. 4 with respect to the neck of the patient.
Figure 6:
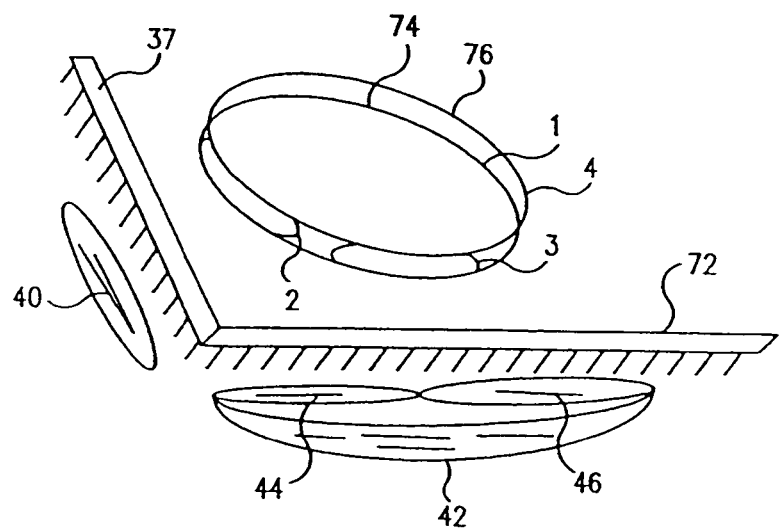
FIG. 6 is a side view of the coil structure illustrated in FIG. 4 showing the positioning of the coil relative to the patient's neck.

While FIGS. 4-5 suggest that loops 1-4 lie in the same plane, other configurations for loops 1-4 are contemplated by the present invention. For example, as shown in FIG. 6, it is desirable to orient loops 2 and 3 in separate planes so that the area of increased magnetic field strength created at the area between loops 1 and 2 and between loops 2 and 4 is targeted toward geniohyoid muscle 40 when the collar is positioned on the patient. Similarly, the area of increased magnetic field strength created at the area between loops 1 and 3 and between loops 3 and 4 is targeted toward the sternothyroid 46, sternohyoid 42 and thyrohyoid 44 muscles. Thus, loop 2 and the upper portions of loops 1 and 4 adjacent to loop 2 are generally parallel the surface of the neck under the patient's chin 37, while loop 3 and the lower portions of loops 1 and 4 adjacent to loop 3 are generally parallel to the portion 72 of the patient's neck between chin 37 and the sternum when the collar is worn by the patient. Please note that FIG. 6 does not illustrate portions of the collar, other than coil 56, for ease of illustration.

Because energizing coil 56 tends to cause heating of the coil, it is also desirable to position portions 74 and 76 of loops 1 and 4, respectively, which are not adjacent loops 2 and 3, as far as possible from the surface of the patient. Increasing the distance from portions 74 and 76 of loops 1 and 4 to the surface of the patient maximizes the thermal protection afforded by the collar, so that as little heat as possible is transferred to the patient. In addition, locating portions 74 and 76 of loops 1 and 4 as far as possible from the patient's skin minimizes the possibility of unwanted stimulation of nerves, such as the phrenic nerve, which contracts the diaphragm, and the vagus nerve, which depresses the patient's heart rate, by the magnetic fields generated by the coil. The configuration of the coil concentrates the magnetic fields in the areas shown in FIG. 4. At all other areas, the field strength is minimized so that the only significant stimulation takes place at the targeted locations.

Figure 7A:
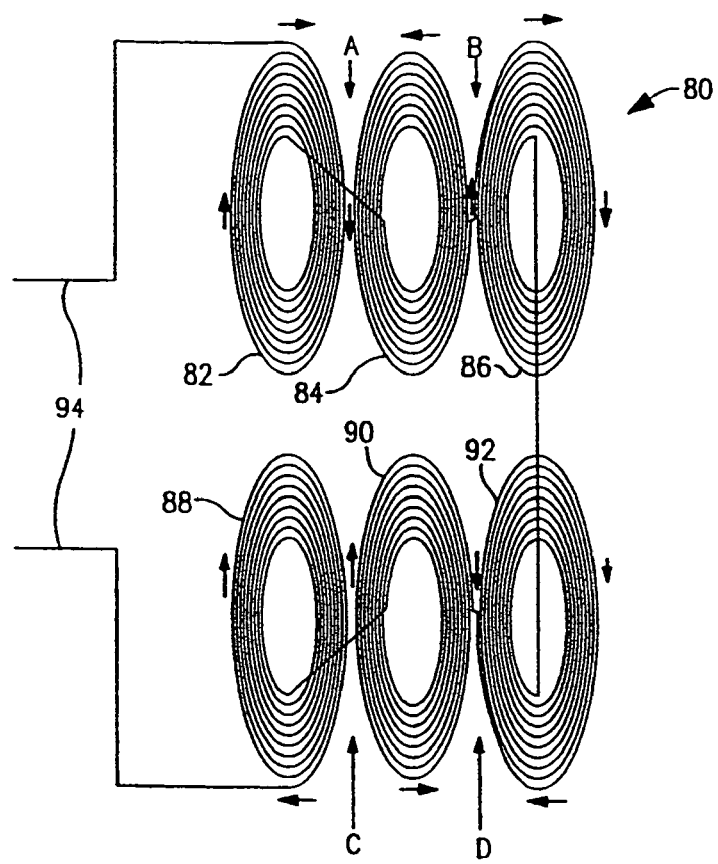
FIGS. 7A, 7B and 7C illustrate a second, third and fourth embodiment, respectively, for the coil in the collar portion of the magnetic stimulator.

A second embodiment for the coil used in the collar according to the principles of the present invention is shown in FIG. 7A. In this embodiment, six generally similar loops 82, 84, 86, 88, 90 and 92 define coil 80 with a current passing therethrough as indicated by the arrows. In the illustrated embodiment, loops 82, 84, 86, 88, 90 and 92 have the same number of turns and are wound from a continuous electrical wire. Because the loops in coil 80 are connected in series, a single pair of terminals 94 are all that is required to energize the coil. The coil configuration illustrated in FIG. 7A provides generally the same magnetic field pattern as the coil configuration illustrated in FIGS. 4-6. Namely, four magnetic field concentrations of generally uniform magnitudes are provided generally at areas A, B, C and D when a current is provided to terminal 94.

Figure 7B:
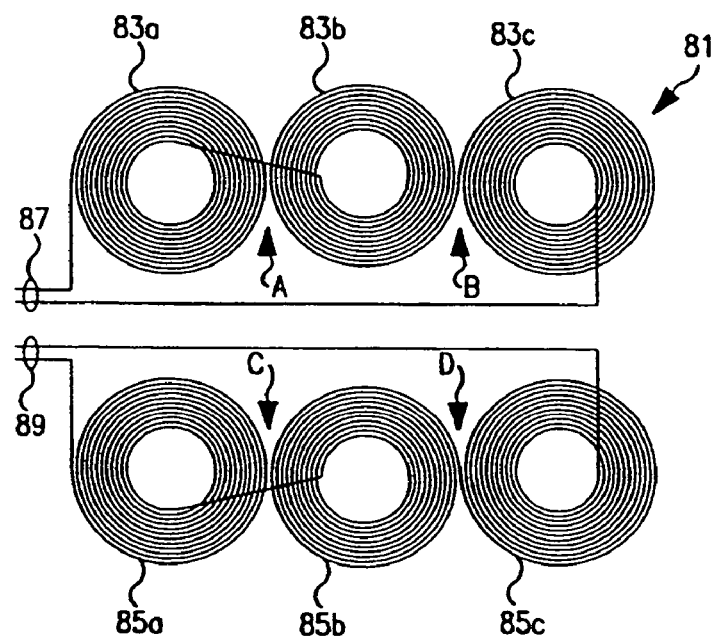

As noted above, the plurality of loops in coil 56 of FIG. 4 and in coil 80 of FIG. 7A are defined from a continuous wire so that only one pair of leads is connected to the power supply. The same current flows through each loop. It is to be understood, however, that it is not necessary for each loop in the overall coil to be connected to any other loop. For example, in an alternative embodiment of the present invention illustrated in FIG. 7B, coil 81 is defined by six loops separated into two groups of loops 83a-83c and 85a-85c, wherein each group of loops is made from a continuous length of wire and is energized by an independent power supply.

As with the previous embodiments, four areas of increased magnetic field concentrations A-D are created by energizing loops 83a-83c and 85a-85c. Loops 83a, 83b and 83c have a common terminal 87, and loops 85a, 85b and 85c have a common terminal 89. As noted above, terminals 87 and 89 can be connected to separate power supplies, i.e., driven by separate currents, so that each group of loops is energized independently of the other, both in terms of timing and magnitude. Alternatively, terminals 87 and 89 can be connected together so that each group of loops receives the same current. This third embodiment of the coil simplifies the manufacture of the coil by enabling each group of loops to be made individually and combined to define the coil, thereby avoiding the relatively complicated winding pattern required to manufacture the coil illustrated in FIGS. 4 and 7A.

Figure 7C:
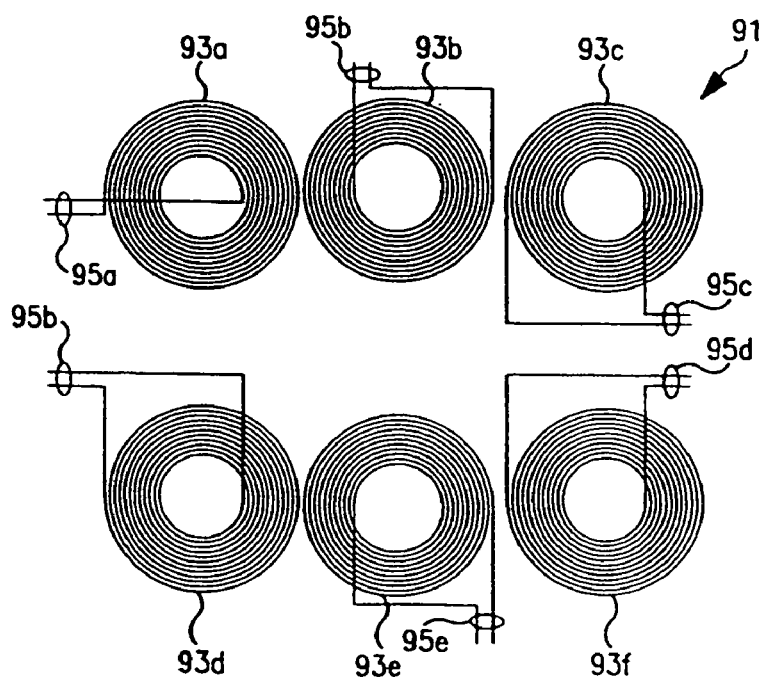

FIG. 7C illustrates a fourth embodiment in which each loop 93a-93f in coil 91 is independent of the other loops in that coil so that each loop 93a-93f has its own terminal 95a-95f, respectively. Because each loop is capable of being energized individually, this configuration maximizes the variety of patterns of increased areas of magnetic stimulation that can be created by coil 91, the intensity of the stimulation at each area, and the timing at which these areas are stimulated, all of which is done under the control of the control unit.

It is to be understood that each loop need not have the same number of turns or be energized at the same voltage/current or at the same time as the other loops or other groups of loops. Instead, the desired magnetic field pattern can be selected by adjusting these parameters so that specific muscles are targeted for stimulation and are stimulated at a specified timing. For example, if there is an area that should be stimulated with a larger intensity than the other areas, the number of turns in the loops associated with that area can be increased, with the current level being kept constant, or the current level to the loops associated with that area can be increased, with the current levels provided to the other loops remaining unchanged. If there is an area that is to be stimulated before the other areas, current can be provided to the loops or group of loops associated with that area prior to being provided to the other loops. If groups of loops are provided, rather than individual loops, the groups of loops can be powered at different levels by associated power supplies, have numbers of turns that are different from other groups of loops, and/or configurations that are different from other groups of loops, and be energized at timings different from the other groups of loops to achieve a variety of magnetic field intensities, patterns and timings.

For example, the coil structure in FIG. 4 can be modified so that loops 1 and 4 are energized together and so that loops 2 and 3 are energized independently of one another. This configuration permits loops 1, 2 and 4 to be energized as a group to stimulate areas A and B. Similarly loops 1, 3, and 4 can be energized as a group to stimulate areas C and D. Also, the timing at which each areas A-D are stimulated can be synchronized or independent so that one area or more areas are stimulated at the same time, at an offset time period or at different times than the other areas.

It can be appreciated that a wide variety of loop configurations, activation combinations or patterns, activation timings and stimulation intensities can be provided so that a single coil structure, such as those shown in FIGS. 4-7C, can provide many different magnetic field patterns. The different magnetic field patterns can be created by independently modulating the electrical current magnitude, phase, and duration, in each loop or groups of loops in the coil. The control unit is used to set the energizing pattern, magnitude and timing for the coil so that selected loops are activated at selected power levels at appropriate times to produce a particular magnetic field pattern with a particular stimulation intensity at selected portions of that pattern. Ideally, the magnetic field pattern, stimulation intensities and stimulation timing targets the muscles in the patient that maximize the OSA treatment capabilities of the present invention.

Figure 8A:
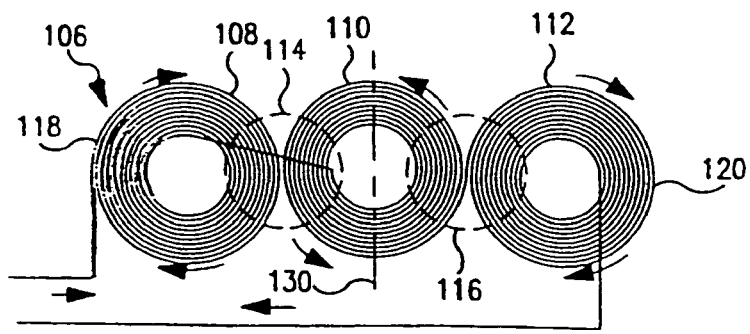
FIGS. 8A and 8B illustrate a fifth embodiment and FIG. 8C illustrates a sixth embodiment for the coil in the collar.
Figure 8B:
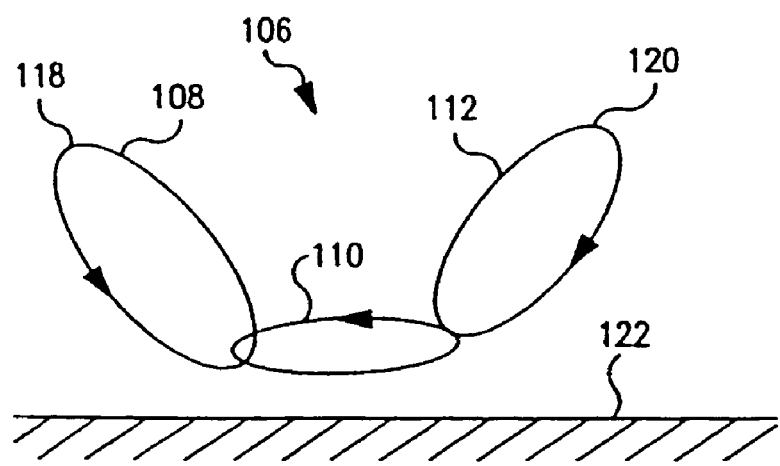

A fifth embodiment of the coil is shown in FIGS. 8A-8B. In this embodiment, coil 106 is defined by three adjacent loops 108, 110 and 112 with the current flowing therethrough as illustrated by the arrows. This configuration provides two areas 114 and 116 of concentrated magnetic stimulation. However, this configuration is more compact than the coil configurations of the previous embodiments. As shown in FIG. 8B, ends 118 and 120 of outer loops 108 and 112 are spaced apart from a surface 122 of the patient to minimize heat transfer to the patient and prevent the magnetic fields from stimulating the phrenic and/or vagus nerves.

As with the previous embodiments, the loops shown in FIGS. 8A and 8B can be wound as a group of individually so that each loop is independent of the other loops. Also, the loops can be energized together from a common source, in groups, or individually and can be energized at the same or different power levels and at the same time or at different times depending on the desired magnetic field pattern.

Figure 8C:
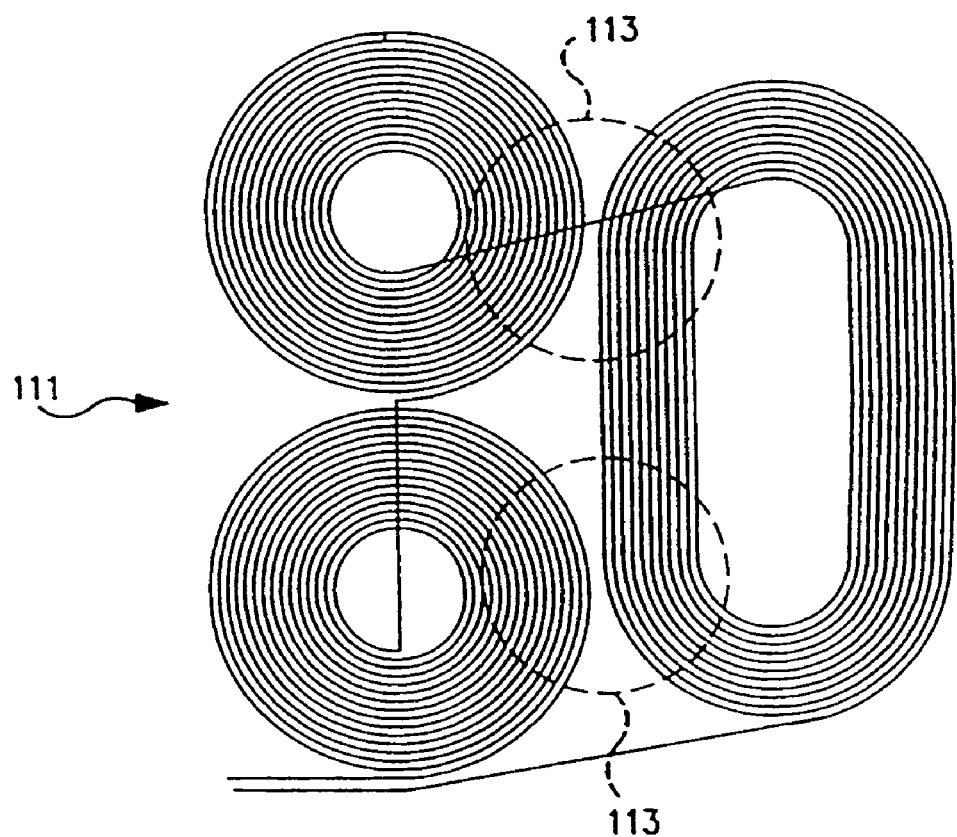

FIG. 8C illustrates a sixth embodiment for the coil. Coil 111 in this figure is similar to the coil configuration shown in FIGS. 4-6 except that one of the large loops have been deleted, leaving a three-loop coil with two areas 113 of field strength summation. This coil configuration is advantageous in that it reduces the coil resistance and inductance as compared to the coil of FIGS. 4-6.

It is to be understood that loop shapes, other than those shown in FIGS. 4, 7A-7C and 8A-8C are contemplated by the present invention. For example, one or more of the loops in the same coil can be circular, elliptical, square, triangular, or rectangular. Also, the present invention contemplates providing more than one coil in the collar. Each such coil can have an overall shape, loop configuration, power supply, and activation pattern (including activation timings and intensity) that differs from the other coils in the collar.

Figure 9:
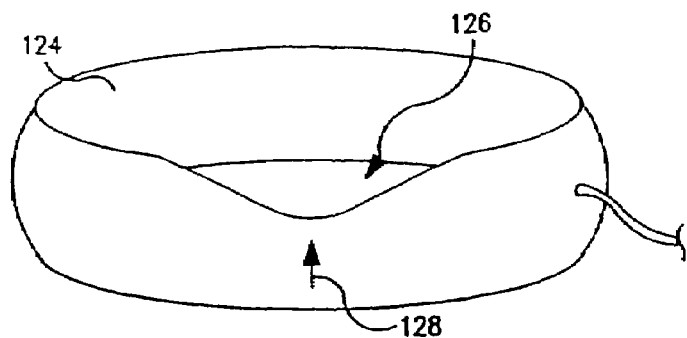
FIG. 9 illustrates an alternative embodiment for the collar.

FIG. 9 illustrates a second embodiment for the collar. In this embodiment, collar 124 includes a cutout portion 126 in the area of the collar underlying the patient's chin. Cutout potion 126 provides a cavity that receives the chin and/or jaw when the collar is positioned on the patient so that the collar is comfortable to the patient.

While collar 34 in FIG. 1 and collar 124 in FIG. 9 are both illustrated as having a generally circular shape with a uniform height and thickness around the circumference (except for the chin cutout in FIG. 9), it is to be understood that other variations in the structure of the collar are contemplated by the present invention. For example, the height and thickness of the collar can be reduced at the back of the patient's neck because this portion of the collar does not directly support the coil in the collar. In addition, the collar can be made from a continuous piece of material that slips over the patient's head with an elastic portion to ensure that the collar remains properly positioned on the patient. Alternatively, the collar can be a strip of material having ends that selectively secure to one another to attach the collar about the patient's neck. In which case, any conventional fastening device, such as snaps, clasps, hooks, a zipper, a button or VELCRO™, can be used to attach the ends of the collar to one another.

It is important that the collar be properly positioned on the patient. To that end, collar 124 in FIG. 9 includes markings 128 on an exposed surface thereof to assist in properly positioning the collar on the patient. In the illustrated embodiment, collar 124 includes an arrow 128 that indicates the central axis of the coil configuration, such as central axis 130 in FIG. 8A, which is the axis of symmetry for the coil configuration. To properly position the coil relative to the muscles to be stimulated, the user aligns arrow 128 directly below the chin along the centerline of the face. It is to be understood that other indicia or indexing markings or mechanisms can be employed to position the collar on the neck at the proper location. For example, markings on the collar could be provided on the portions of the collar that overlie the carotid arteries when the collar is positioned on the patient. The location of the carotid arteries are relatively easy to locate, either by the user or another person applying the collar and, thus, are useful in positioning the collar merely by aligning the carotid artery markings on the collar with the patient's carotid arteries.

Figure 10:
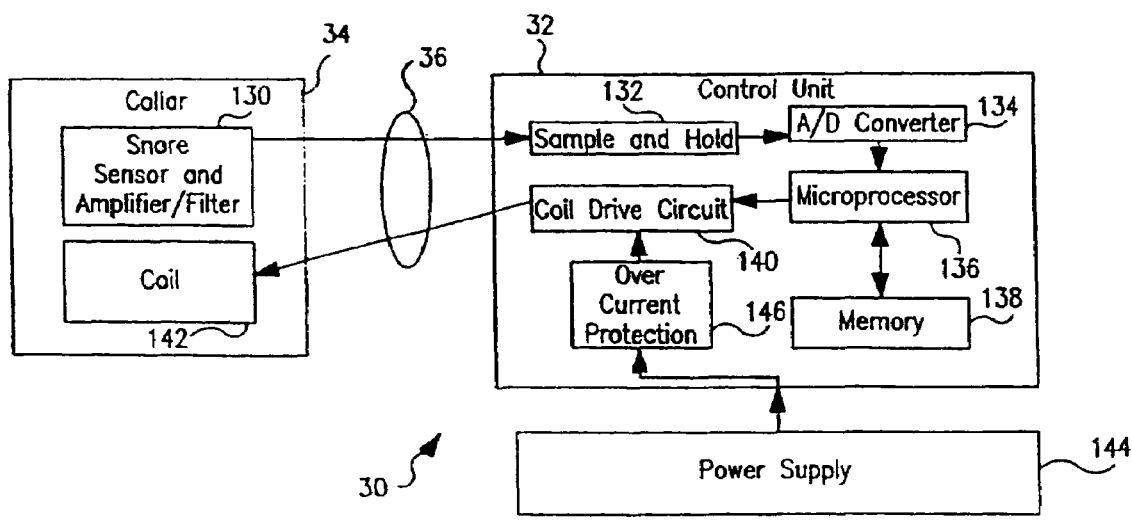
FIG. 10 is a schematic diagram of the magnetic stimulator illustrated in FIG. 1.

FIG. 10 is a schematic diagram of magnetic stimulator 30. In the illustrated embodiment, collar 34 includes a snore sensor 130, such as sensor 58 of FIG. 3, and circuitry for amplifying and filtering the analog signal output by the sensor. Filtering is done to eliminate extraneous noise from the signal output from the snore sensor. The amplified and filtered snore sensor signal is provided to sample and hold sensor 132, A/D converter 134 and microprocessor 136 in control unit 32. Microprocessor 136 controls the operation of a coil drive circuit 140, which provides energy to coil 142 in collar 34. Memory 138 stores threshold data, data provided from microprocessor 136, and programs carried out by the microprocessor. Power from a power supply 144 is provided to coil drive circuit 140 through an over current protection circuit 146. Power supply 144 can be any suitable power supply that is capable of providing sufficient power to coil 142. Coil drive circuit 146 can be any suitable circuit for energizing coil 142, such as a selectively dischargeable capacitance. Over current protection circuit 146 can be any suitable circuit that limits the amount of energy (voltage/current) that can be provided to coil 142 for safety purposes.

The energy limiting function of over current protection circuit 146 is separate from the energy level setting function of microprocessor 136. More specifically, over current protection circuit 146 ensures that the patient is never stimulated at a level that is above that appropriate for that patient, even if the maximum stimulation intensity level is set by the user. Preferably, the maximum current permitted by over protection circuit 146 is set in advanced based on the characteristics of the patient using the stimulator.

Figure 11:
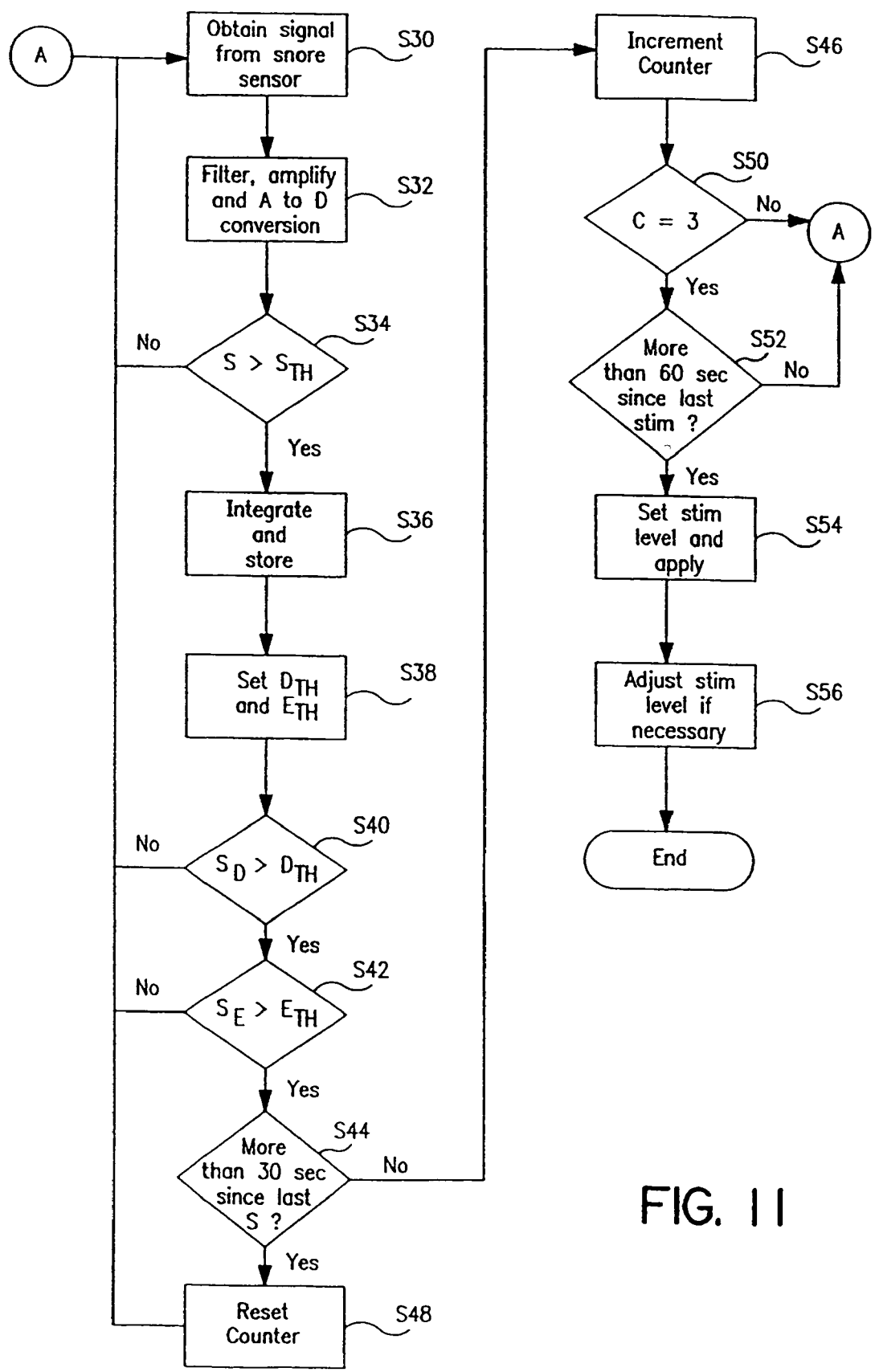
FIG. 11 is a flowchart illustrating a process carried by the magnetic stimulator in achieving its therapeutic effect.

One embodiment of the operation of magnetic stimulator 30 is discussed below with reference to FIG. 11, which is a flowchart illustrating a process carried by the magnetic stimulator in achieving its therapeutic effect. More specifically, the process illustrated in FIG. 11 is repeatedly conducted under the control of the microprocessor once the magnetic stimulator is activated. In step S30, the airway sound vibrations are detected using an appropriate transducer that is in communication with the patient's airway, such as audio snore sensor 58 of FIG. 3. These sound vibrations are output by the transducer as an electrical signal, which is bandpass filtered, amplified and converted from an analog to a digital signal S in step S32. Filtering is performed to eliminate noise in the signal output from the sensor, and amplification is performed to adjust the signal level to a level suitable for the components receiving that signal. Signal S is provided to microprocessor 136.

In step S34, the magnitude of signal S is compared to a threshold magnitude $S_{TH}$, which is a predetermined minimum noise threshold. Threshold magnitude $S_{TH}$ is preferably determined and set so in advance so that it is specific to the patient using the magnetic stimulator. If signal S does not exceed $S_{TH}$, the signal output by the transducer is considered to not correspond to a snore and the process returns to step S30. If signal S exceeds $S_{TH}$, the signal is considered to correspond to a snore sound and is integrated in step S36 to determine its duration $S_D$ and energy level $S_E$, which are stored in memory 138.

In step S38, duration and energy level thresholds $D_{TH}$ and $E_{TH}$, respectively, are set. These thresholds can have fixed values that are determined and set in advance, preferably based on the condition of the patient, or they can have values that vary during the operation of the stimulator. For example, the magnitude of duration and energy level thresholds $D_{TH}$ and $E_{TH}$ can be set based on the recent history of snore sounds. During an intense snoring period, the energy level thresholds $D_{TH}$ and $E_{TH}$ can be increased so that lower amplitude snore sounds. On the other hand, these threshold values can be decreased, thereby increasing the sensitivity of the stimulator, if apnea events are detected or if the intensity (magnitude and/or duration) of the snore sounds diminish.

In a preferred embodiment of the present invention, an average of a predetermined number of previous signals corresponding to snore sounds are used to set thresholds $D_{TH}$ and $E_{TH}$. For example, the duration and energy level of the past ten snore sound signals, eliminating the maximum and minimum values, can be averaged to set these thresholds. It is to be understood, however, that other techniques can be used to average the previous snore sounds signals to set $D_{TH}$ and $E_{TH}$.

In steps S40 and S42, the duration $S_D$ of the snore sound signal is compared to duration threshold $D_{TH}$, and the energy level $S_E$ of the snore sound signal is compared to energy level threshold $E_{TH}$. If either of these thresholds are not met, the process returns to step S30, meaning that the snoring sound does not qualify as an apneic event. If, however, both of these thresholds are met, the snore sound signal is considered to qualify to an apneic event and the process continues to step S44.

In step S44, microprocessor determines if more than 30 seconds have elapsed since the last snore sound signal S qualifying as an apneic event. If it has been 30 seconds or less since the last snore sound signal S qualifying as an apneic event, a counter in microprocessor 136 is incremented in step S46. Thus, the counter is incremented if the upper airway sound producing a sound signal that qualifies as an apneic event is detected at or within 30 seconds of a previous sound signal also qualifying as an apneic event. If more than 30 seconds have elapsed, this counter is reset in step S48 and the process returns to step 30.

In step S50, the microprocessor determines if the counter has reached three. If not, the process returns to step S30. If so, the microprocessor determines, in step S52, if more than 60 seconds have elapsed since the previous stimulation. If only 60 or less seconds have elapsed since the previous stimulation, the process returns to step S30. If, however, more than 60 seconds have elapsed, the stimulation level is set by the microprocessor in step S54 and the microprocessor causes coil drive circuit 140 to apply energy to the coil to stimulate the patient at the set stimulation level.

The initial stimulation level is typically set in advance by a qualified physician. However, an input device, such as dial or keypad, on or operatively coupled to the control unit can be used to adjust this level. Preferably, a lockout mechanism is provided to prevent the user from adjusting the intensity level beyond that specified by the physician. For example, the control unit can be preprogrammed, prior to being provided to the user, to not accept or apply any stimulation levels above a predetermined level. Thus providing a further safeguard against excessive stimulation.

The present invention also contemplates modifying the intensity of the magnetic stimulation as necessary during the stimulation therapy. This is done in step S56 following the application of the magnetic stimulation using a feedback system. For example, as additional upper airway sounds qualify as snore sounds or further qualify as an apneic events, the intensity of the magnetic stimulation can be increased, preferably incrementally, to further stabilize the airway. The incremental amount of each increase can be fixed or variable, and each increase need not be by the same amount. The amount of the incremental increase is typically established in advance or it can be set based on the conditions of the patient, such as the snoring activity. In a preferred embodiment of the present invention, steps S30 through S50 are repeated, and if the counter has reached three in step S50, the stimulation level is increased by a predetermined amount.

The stimulation level can also be decreased if the number of upper airway sounds qualifying as snore sounds or further qualifying as apneic events decreases following the onset of stimulation. In this manner, only the stimulation intensities necessary to treat the apneic events are applied to the patient, thereby conserving power and minimizing use of the magnetic stimulator.

In a preferred embodiment of the present invention, if no apneic event snore sounds are detected after 5 minutes after the onset of stimulation, the stimulation level is reduced by a first predetermined amount, which can either be fixed or variable. In a second embodiment of the present invention, steps S30 through S50 are repeated and if the counter does not reach three in step S50, the stimulation intensity is reduced by the first predetermined amount. In both of these embodiments, the stimulation intensity can be further reduced by a second predetermined amount for each consecutive time period, such as a 5 minute interval, during which no apneic events are detected until the stimulation level reaches zero. This second predetermined amount can be the same as the first predetermined amount and can be fixed or variable. Thereafter, the process returns to step S30.

It is to be understood, that the time period during which further apneic events are monitored to determine how to change (or cease) the stimulation level, if necessary, can be a fixed or variable length of time. Also, the present invention contemplates simply ceasing stimulation after a predetermined period of time has elapsed during which a minimum number, e.g., zero, of apneic events are detected. It is to be further understood that this same scenario for decreasing the intensity of the magnetic stimulation can also be used to increase its intensity.

While the occurrence of an apneic event is detected in step S50 if the counter reaches three, it is to be understood that other integer numbers of sounds qualifying as a snore sound can be used as a benchmark for determining the occurrence of an apneic event. For example, two or four snore sounds occurring within a predetermined time period can be used to determine the occurrence of an apneic event. Furthermore, the duration of this predetermined time period, which corresponds to the 30 sec period in step S44, can be set in advance or it can be variable based on the monitored conditions of the patient.

Although the initiation, modification and termination of stimulation can be conducted using the process discussed above, it is also possible to apply the process discussed in U.S. Pat. No. 5,203,343, the contents of which are incorporated herein by reference, to the magnetic stimulator. The process illustrated in the '343 patent is intended for use with a positive airway pressure device to control the initiation, modification and termination of the positive airway pressure. However, the process taught by the '343 patent can be used in an analogous manner to control the magnetic stimulator. In which case, it is not the pressure level that is controlled, but the intensity of the magnetic stimulation.

The initiation, modification and termination of stimulation can also be performed based on the patient's respiratory cycle. For example, stimulation can be synchronized with the patient's inspiration so that stimulation begins at the same time as inspiration. Alternatively, stimulation can be initiated just prior to, i.e., not more than one second before, or just after, i.e., not more than one second after, the initiation of inspiration. This method obviates the need to determine the occurrence of snore and/or an apneic event and attempts to eliminate such events before they occur.

In an exemplary embodiment of the present invention, stimulation energy is provided to the patient by energizing the coil with a series of current pulses, each pulse having a prescribed magnitude and duration. The magnitude of the pulses in the pulse train and/or the duty ratio can be set to determined the overall intensity of the stimulation provided to the patient. For example, in a preferred embodiment, a series of pulse trains, each having a pulse rate between 5-30 pulses/sec and lasting between 1-3 seconds, is provided to the patient. Alternatively, stimulation can be provided in phase with the patient's inspiratory effort. This requires monitoring the inhalation and exhalation of the patient using any appropriate device and timing the stimulation to coincide with the onset of inhalation. It is to be understood, however, that stimulation can be initiated at any period offset from the onset of inspiration so that the initiation of stimulation either precedes or follows the onset of inspiration.

Maximum magnitudes and pulse repetition rates can be set in advance to limit the overall stimulation that the patient receives. Typically, these magnitudes and pulse repetition rates, as well as the duration of the pulse trains, threshold levels and other variables discussed above are set by a doctor or other physician after conducting an evaluation of the patient. Furthermore, the current pulses are optimized to reduce the energy dissipated in the coil. For example, the coil is energized by a current emanating from charge stored on a low-loss capacitor, most of which charge is recaptured during the applied pulse.

Although not shown in the process illustrated in FIG. 11, the overall energy level provided to the coil can be ceased or reduced if the coil temperature exceeds a predetermined value. Conversely, the energy level can be increased so long as the coil temperature remains within an acceptable range. This feature of the present invention ensures that the patient's safety is not compromised while still providing the maximum therapy to the patient.

The present invention further contemplates controlling the application, changes in intensity, and cessation of stimulation based on other criteria. For example, the present invention contemplates delaying the application of stimulation energy to the patient after the magnetic stimulation system has been activated, so that the patient has the opportunity to fall asleep prior to the start of the stimulation therapy. This can be accomplished, for example, by causing a timer to be activated, either manually or automatically upon activation of the stimulation system, and once the time counts out a predetermined time interval, initiating the stimulation therapy. This therapy delay feature can also be based on a conventional clock so that the user can set the therapy to begin at any preselected time during the night.

Similarly, the magnetic stimulation system of the present invention can cease application of the stimulation after the passage of a selectable time period so that stimulation ceases before the patient typically awakes, thereby preventing the user from being awaken by the stimulation therapy. This delay in turning off the stimulation therapy can be based on a time interval or based on a conventional clock.

The present invention also contemplates controlling the stimulation energy applied to the patient in a variety of ways to maximize patient comfort. For example, one embodiment of the present invention contemplates incrementally increasing the intensity of the stimulation energy being delivered to the patient following the actuation of the stimulation system. This increase can take place in place of or after the delay period discussed above. Another embodiment of the present invention contemplates incrementally decreasing the intensity of the stimulation energy being delivered to the patient. This decrease can take place in place of or before the delay in turning off the stimulation therapy discussed above. The intensity of the stimulation can also be controlled based on the patient's sleep stages, assuming, of course, that the appropriate sensors and control systems are provided to detect and classify the patient's sleep stages.

The present invention further contemplates providing various methods for interrupting the stimulation therapy. For example, a pause function that stops stimulation therapy can be initiated by the user either by manually actuating an input device, such as a button, on the control unit or remotely. The stimulation therapy can also be interrupted automatically, if, for example, a malfunction is detected. Restart of the stimulation therapy can begin automatically, after the elapse of a fixed or selectable time period, for example, or by manually actuating the input device, i.e., again actuating the button or the remote control. Restart of the stimulation therapy can begin at the stimulation energy levels existing prior to the pause, at the initial energy level, or at some other preselected level. In addition, the delay function and/or the incremental intensity functions can be instituted during the restart so that the user again has the opportunity to fall asleep in the absence of any stimulation therapy.

The present invention also contemplates providing a safety feature in which a maximum stimulation energy that can be provided to the patient is set. This can be accomplished via a control unit. This stimulation energy provided to the patient will not exceed the set maximum regardless of the stimulation energy set by the user on the control unit. It is preferable that the means by which the maximum stimulation energy is set is secured so that it cannot be altered inadvertently, or tampered with. The use of a password that must be input in order to alter the maximum setting is an example of such a security feature.

In still another embodiment of the present invention, the magnetic stimulation system is provided with an automatic turn-on and/or an automatic turn-off feature. This provides the advantages of simplifying the operation of the system and conserving power, for example. Sensors on the collar, such as a temperature sensor or galvanic type sensor, can detect when the appliance is disposed on the patient. The output of these sensors is used to control the actuation and deactivation of the stimulation system or the application and cessation of the stimulation therapy.

With the growing popularity of managed healthcare, healthcare providers are becoming more concerned that the patients actually use the prescribed therapy devices. To meet this concern, the present invention monitors patient compliance by storing information regarding the used of magnetic stimulator, such as the amount of time that the unit was turned on and/or the amount of time that the coil has been energized.

In one embodiment discussed above, the coil is only energized once an apneic event is detected. In another embodiment, the coil is energized in synchronization with the patient's respiratory cycle. Thus, the present invention makes it difficult for the patient to deceive the healthcare provider as to the actual usage of the device, thereby providing a relatively reliable and accurate indication of the actual usage of the magnetic stimulator.

Furthermore, because the stimulator is capable of communicating with external devices using a modem, for example, patient compliance can be remotely monitored by the healthcare provider with little or no patient involvement. This same remote patient compliance monitoring feature also permits the healthcare provider to monitor the operating status of the stimulator, for example, by causing the device to run a diagnostic routine and reports the results.

Figure 12:
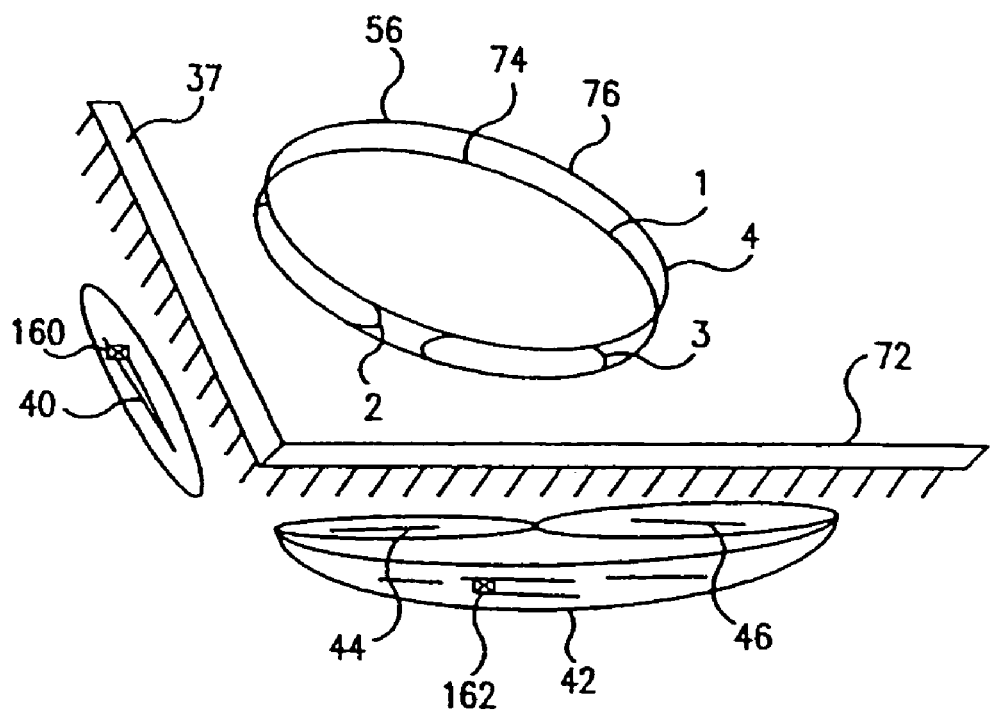
FIG. 12 is a side view of the coil, a portion of the patient's neck, and a miniature intramuscular stimulator according to another embodiment of the present invention.

FIG. 12 illustrates a further embodiment of the present invention. In this embodiment, the structure for the magnetic stimulator, including the coil and control unit are the same as in the previous embodiments. In this embodiment, however, miniature implantable intramuscular stimulators 160 and 162 are provided in or near the patient's muscles that are targeted for stimulation or near the nerves that contract such muscles. Because these devices are relatively small, they can be implanted using a hypodermic, thereby minimizing the invasiveness of the implantation surgery. Also, because these devices are not physically connected to any other devices, they do not suffer the medical consequences associated with providing an electrode permanently penetrating the patient's skin, as is the case with many conventional implanted electrodes.

Figure 13:
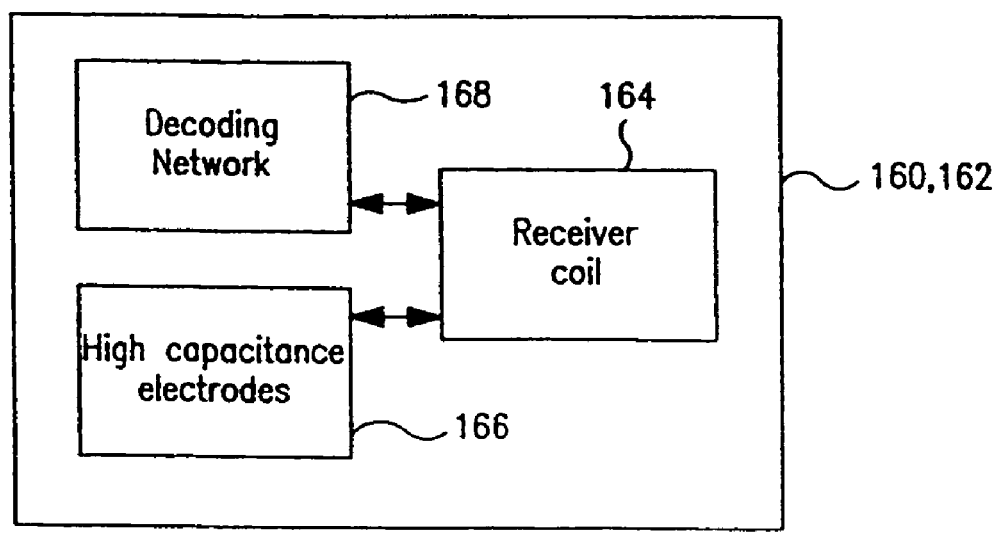
FIG. 13 is a schematic diagram of the miniature intramuscular stimulator adapted for use with the magnetic stimulator of the present invention.

As shown in FIG. 13, intramuscular stimulators 160 and 162 include a receiver coil 164 that communicates with coil 56 in the collar, high capacitance electrodes 166, and a decoding network 168. Receiver coil 164 and high capacitance electrode 166 transfer the magnetic energy provided by the coil into electrical energy that is applied directly to the muscle (or nerve) contacting the intramusculuar stimulator. This permits specific muscles to be targeted for stimulation, which is especially beneficial in situations where the targeted muscle is recessed deeply beneath the patient's skin or is not easily distinguishable from non-target muscles of nerves.

Decoding network 168 enables the control unit to distinguish and control a selected intramuscular stimulator using, for example, an AM or FM signal. In this manner, intramuscular stimulator 160 can be controlled, for example, to stimulate the geniohyoid muscle without causing intramuscular stimulator 162 to stimulate the sternohyoid muscle. Of course, other muscles can be target using other intramusculor stimulators and groups of muscles (or one muscle) can be stimulated using a plurality of intramuscular or stimulators implanted into those muscles (or that single muscle) all of which have the same identification for activation purposes. The stimulation intensities and the timing at which the muscles are stimulated can be varied in the same manner discussed above with respect to the many ways in which areas A-D can be stimulated. See FIG. 4. This is accomplished by selectively actuating the intramuscular stimulators either independently of one another or in synchronization and controlling the stimulation intensity level of each intramuscular stimulator, all of which is done by the control unit.

Figure 15:
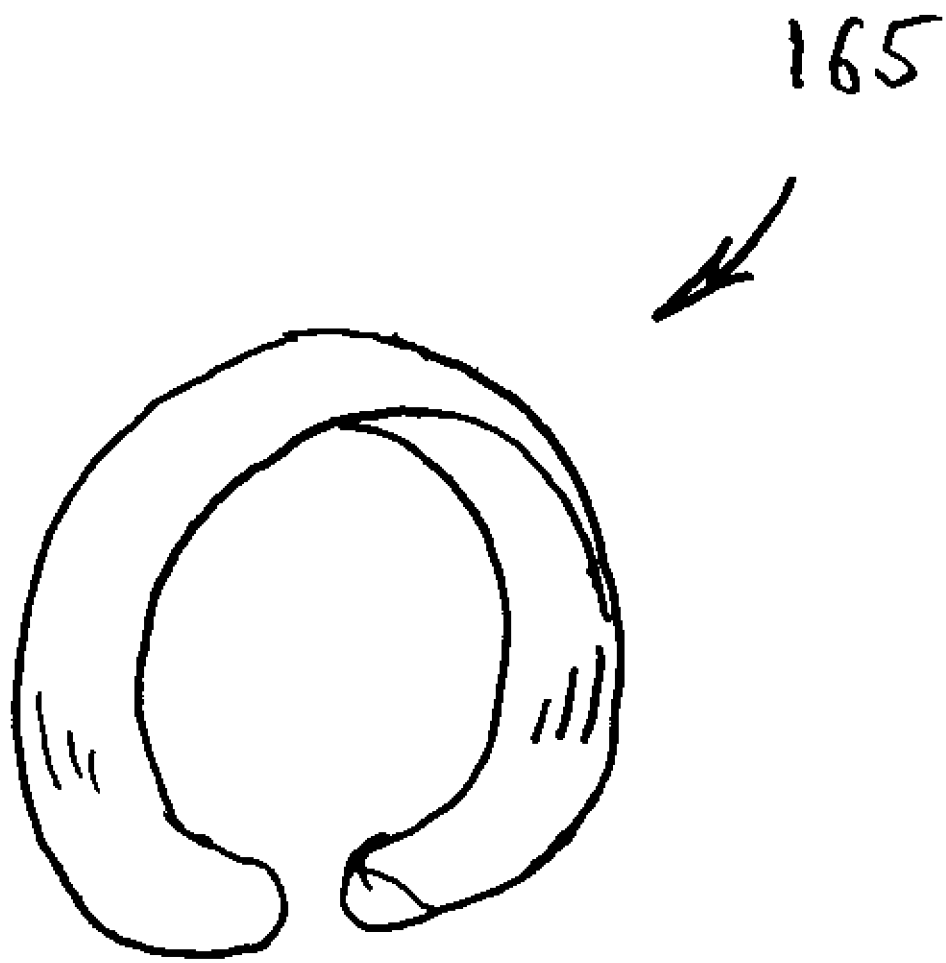
FIG. 15 is a perspective view of a implantable passive probe according to the principles of the present invention.

The present invention also contemplates providing an implantable passive probe 165 that alters the magnetic field strength in the vicinity of the probe in addition to or in place of the active probes discussed above. In a preferred embodiment of the present invention, as illustrated in FIG. 15, passive probe 165 is a glass encapsulated strip of material having a high magnetic permeability, typically about 0.5 mm in length and 2 mm long, and curved so that the strip can wrap, at least partially, around a nerve. Such a device having a high magnetic permeability reduces the magnetic field at its exterior. Providing such a device near a nerve fiber enhances magnetic stimulation by creating an increase in the gradient of the electric field along the nerve fiber. This electric field gradient is believed to be the mechanism by which the nerve fiber is stimulated.

From the forgoing, it can be appreciated that the present invention increases the tension in the muscles that stabilize the upper airway to prevent its collapse. It is non-painful and more tolerable than skin/surface stimulation techniques. The device is non-invasive, and, therefore, safer than systems that stimulate the musculature with implanted electrodes. For those patients for whom electrical stimulation of the muscles stabilizing the upper airway is planned, magnetic stimulation may be useful in establishing the efficacy of the planned treatment. In this regard, the intensity of the magnetic stimulation applied by the qualified caregiver can be larger than that possible in the unit intended for home use. This enables the caregiver to determine if electrical stimulation, either induced by the present invention or using conventional implanted electrodes, will produce the desired therapeutic benefit in that patient.

In the previous embodiments of the present invention, the magnetic stimulating system is the sole means for treating the patient's breathing disorder. It is to be understood, however, that the present invention contemplates using the magnetic stimulating system in conjunction with other techniques for treating breathing disorders. For example, one embodiment of the present invention contemplates using the magnetic stimulating system in conjunction with conventional electrical stimulation systems to target additional muscles or muscle groups for stimulation or supplement the stimulation provided by the electrode-based muscle stimulator.

Another embodiment of the present invention contemplates using the magnetic stimulating system in conjunction with a conventional pressure support system that applies positive air pressure at the mouth and/or nose of the patient to "splint" the airway. Even if magnetic stimulation of the muscles of the airway does not fully open the airway, it is believed that the induced muscle stimulation will reduce the pressures necessary to be provided by the pressure support system in order to splint the airway and treat the breathing disorder. It is well recognized that the pressure needed to be provided to the patient by the pressure support device to treat the breathing disorder should be kept as low as possible.

The present invention contemplates that the magnetic stimulating system of the present invention can be used in conjunction with most, if not all, conventional pressure support systems. Such pressure support systems typically include a pressure generator 172 that generates. a gas flow, a conduit 173 that carries the gas flow to the patient, and a patient interface device 174 that communicates the conduit with the patient's airway. See FIG. 14. Examples of pressure support devices that are used in conventional pressure support systems include a CPAP (continuous positive airway pressure) device, hi-level devices, which provide variable levels of pressure support during the patient's respiratory cycle, such as the Respironics BiPAP® devices, PAV® devices and PPAP devices. Examples of suitable patient interface devices include nasal masks, oral appliances, nasal/oral masks, full face masks, hoods, nasal cannulas, trachea tube, and any other device that communicates a gas flow with the patient's airway.

The present invention also contemplates using the magnetic stimulator discussed above as a diagnosis device to assess the likelihood that a subject suffers from OSA. It has been clinically determined using standard electromyography techniques that the muscle activity in the upper airway of awake patients suffering from OSA is higher than in normal subjects. By measuring the compliance of the subject in the awake state, both in the presence and in the absence of magnetic stimulation, it is possible to determine whether that subject is likely to suffer from OSA. Compliance is determined by measuring the change in the cross-sectional area, and hence the volume, of the patient's upper airway while different positive pressures are applied to the upper airway by means of a standard continuous positive airway pressure ("CPAP") device.

In patients likely to suffer from OSA, the difference in the measured compliance with and without magnetic stimulation is less than the difference in the measured compliance with and without magnetic stimulation in normal subjects. This is so because patients likely to suffer from OSA tend to have abnormally high muscle activity in their upper airway in the awake state. Thus, the application of magnetic stimulation to the upper airway in the awake state has little effect in tensing the upper airway muscles, resulting in little change in compliance. In normal patients, however, the application of magnetic stimulation to the upper airway generally has a more significant impact on compliance because the magnetic stimulation tenses the otherwise relaxed upper airway muscles. Thus, by measuring compliance, first without magnetic stimulation to the upper airway muscles and then with such stimulation, it can be determined that the subject is likely to suffer from OSA if there is relatively little change in compliance under these two conditions.

Figure 14:
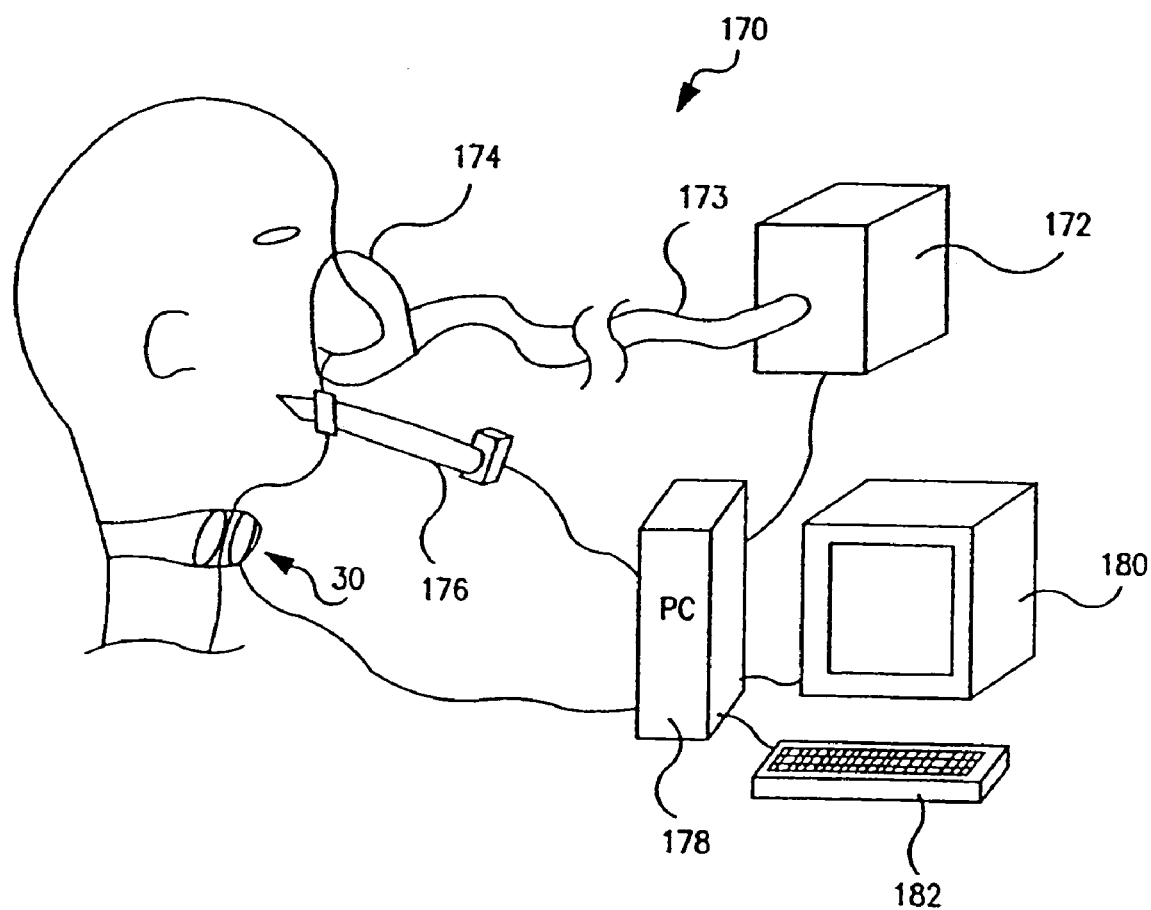
FIG. 14 is a schematic diagram of a system for diagnosing whether a patient is likely to suffer from OSA using the magnetic stimulator.

FIG. 14 illustrates an example of a system 170 for diagnosing the likelihood that a subject suffers from OSA using the magnetic stimulator discussed above. Diagnosis system 170 includes a CPAP device 172 for providing continuous positive airway pressure to the patients airway via a nosemask 174 or other suitable nose sealing member. Magnetic stimulator 30 induces tension in the subjects upper airway muscles. An acoustic transducer 176 measures the subject's compliance, i.e., the change in the cross-sectional area, and hence the volume, of the patient's upper airway. It is to be understood that other devices for measuring the subject's compliance, such as through magnetic resonance imaging (MRI), are contemplated by the present invention. An acoustic transducer is used for this purpose in the illustrated embodiment because of its relative simplicity, ease of use and low cost. In the illustrated embodiment, CPAP device 172, acoustic transducer 176 and magnetic stimulator 30 are all operated under the control of a computer 178. Also, a monitor 180 and keyboard 182 are coupled to computer 178.

System 170 diagnoses the likelihood that the subject suffers from obstructive sleep apnea by first measuring the compliance of the subject to obtain a first compliance level using acoustic transducers 176. This is done in the absence of magnetic stimulation. Next, a magnetic field is applied to at least one muscle group associated with an upper airway of the subject using magnetic stimulator 30. The compliance of the subject is measured while the magnetic field is being applied to obtain a second compliance level. The first compliance level is compared to the second compliance level to determine the difference therebetween. The smaller the difference between the first and second compliance levels, the more likely the subject suffers from obstructive sleep apnea. In a preferred embodiment of the present invention, computer 178 makes this comparison and outputs an indication of the likelihood that the subject suffers from OSA.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A method of treating obstructive sleep apnea comprising:
   implanting a passive probe into target tissue within such a patient, wherein the target tissue corresponds to a location in such a patient where applying an electrical stimulation to such a patient serves to stabilize an upper airway of such a patient without assistance of an implanted device that mechanically suspends tissues associated with the upper airway;
   providing a magnetic field to the passive probe, wherein the passive probe alters a characteristic of the magnetic field to enhance a stimulation of the target tissue of such a patient by the magnetic field, and
   controlling delivery of the magnetic field to the passive via an external controller located outside such a patient.

2. The method according to claim 1, wherein the target tissue includes 1) muscle tissue associated with an upper airway of such a patient or 2) nerves associated with the muscle tissue.

3. The method according to claim 1, further comprising a sensor adapted to be located relative to such a patient so as to detect an apneic event of such a patient, and wherein the controlling step includes providing the magnetic field based on detection of the apneic event.

4. The method according to claim 1, further comprising a sensor adapted to be located relative to such a patient so as to detect a respiratory pattern of such a patient, and wherein said controlling step includes providing said energizing signal based on detection an output of said sensor.

5. The method according to claim 1, wherein the implanting step includes implanting at least two passive probes in such a patient, and wherein controlling delivery of the magnetic field includes controlling which of the at least two passive probes on which the magnetic field is directed.

6. A system for treating obstructive sleep apnea comprising:
   a first passive probe adapted to be positioned within a first target tissue of a patient, wherein the first target tissue corresponds to a location in such a patient where applying an electrical stimulation to such a patient serves to stabilize an upper airway of such a patient without assistance of an implanted device that mechanically suspends of tissues associated with the upper airway; and
   an external controller adapted to produce a magnetic field for delivery to the first passive probe, and where the passive probe is configured and arranged to alter a characteristic of the magnetic field to enhance a stimulation of the target tissue by the magnetic field.

7. The system according to claim 6, wherein said first target tissue includes 1) muscle tissue associated with an upper airway of such a patient or 2) nerves associated with the muscle tissue.

8. The system according to claim 6, further comprising a sensor adapted to be located relative to such a patient so as to detect an apneic event of such a patient, and wherein the controller provides the magnetic field to the first passive probe based on detection of the apneic event.

9. The system according to claim 6, further comprising a sensor adapted to be located relative to such a patient so as to detect a respiratory pattern of such a patient, and wherein the controller provides the magnetic field to the first passive probe based on an output of the sensor.

10. The system according to claim 6, further comprising a second passive probe adapted to positioned within second target tissue of a patient, wherein the second target tissue corresponds to a location in such a patient where applying an electrical stimulation to such a patient serves to stabilize an upper airway of such a patient, and wherein the controller controls delivery of the magnetic field to the first passive probe and the second passive probe.

* * * * *